United States Patent [19]

Seto et al.

[11] Patent Number: 5,272,271

[45] Date of Patent: Dec. 21, 1993

[54] PYRANOBENZOXADIAZOLE DERIVATIVES

[75] Inventors: Kiyotomo Seto; Hiroo Matsumoto; Yoshimasa Kamikawaji; Kazuhiko Ohrai; Keisuke Ohdoi; Ryozo Sakoda, all of Funabashi; Yukinori Masuda, Minamisaitama, all of Japan

[73] Assignee: Nissan Chemical Industries, Ltd., Tokyo, Japan

[21] Appl. No.: 726,897

[22] Filed: Jul. 8, 1991

[30] Foreign Application Priority Data

Jul. 10, 1990 [JP] Japan .................................. 2-182525
May 24, 1991 [JP] Japan .................................. 3-120279

[51] Int. Cl.$^5$ .................. C07D 403/04; C07D 271/12
[52] U.S. Cl. .................................. 546/199; 548/126
[58] Field of Search ................ 546/197, 198, 199; 548/126

[56] References Cited

U.S. PATENT DOCUMENTS 4,900,752 2/1990 Seto ................................... 546/199

FOREIGN PATENT DOCUMENTS 327127 9/1989 European Pat. Off. .

OTHER PUBLICATIONS

Burger, A. "Medicinal Chemistry" 1960 2nd Ed. Interscience Pub. pp. 565, 566, 568, 580, 600, 601.
Hackh's "Chemical Dictionary" 1983 p. 16.

*Primary Examiner*—C. Warren Ivy
*Assistant Examiner*—Celia Chang
*Attorney, Agent, or Firm*—Oliff & Berridge

[57] ABSTRACT

A compound of the formula (I):

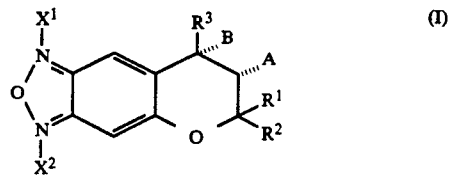

wherein $X^1$ and $X^2$ do not exist or represent oxygen atom; A represents OH or acyloxy group having 1 to 4 carbon atoms; B represents hydrogen atom; A and B together represent a bond; $R^1$ and $R^2$ represent hydrogen atom or alkyl group having 1 to 4 carbon atoms, or $R^1$ and $R^2$ together represent 1,2-ethylene, 1,3-propylene, 1,4-butylene or 1,5-pentylene, and these alkylene groups may be substituted by alkyl group having 1 to 4 carbon atoms; $R^3$ represents amido group of the formula:

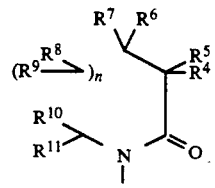

wherein n, $R^4$, $R^5$, $R^6$, $R^7$, $R^8$, $R^9$, $R^{10}$ and $R^{11}$ represent specific groups, and the pharmacological acceptable salts of the compounds which can form salts have strong activity for lowering blood pressure, and process therefor and pharmaceutical use of the compounds.

13 Claims, No Drawings

PYRANOBENZOXADIAZOLE DERIVATIVES

BACKGROUND OF THE INVENTION

The present invention relates to novel pyranobenzoxadiazole derivatives, pharmaceutical compositions containing said derivatives, use thereof for the therapy of hypertension, asthma, cerebrovascular disorder, angina pectoris or incontinence which causes in mammarian animals inclusive of human being or for hair-growth stimulation and a process for producing the above.

Japanese Patent Laid-open Publication No. Sho 58-67683 (67683/1983) discloses that a compound (Development code No. BRL-34916) of the formula (A):

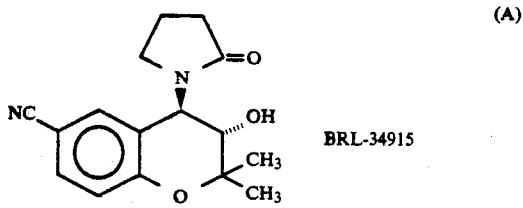

has an activity for lowering blood pressure with respect to spontaneously hypertensive rats.

Br. J. Pharmac. (1986), 88, p.p. 103-111 discloses the possibility that the compound BRL-34915 activates K+ channel and moves resting potential of membrance to the hyper polarization.

Br. J. Pharmac. (1986), 89, p.p. 395-405 shows that the compound BRL-34915 loosens trachealis of guinea pig and suggests that it has utility as a medicine for the therapy of asthma.

Angiology (1987), 27, pp. 425-431 suggests that a composition for activating K+ channel is effective for the treatment of arrhythmia and angina pectoris.

Br. J. Pharmac. (1987), 91, pp. 803-813 shows that the compound BRL-34915 loosens uterus of rats. For this fact, it may be effective for preventing premature delivery.

DLO News ROUND-UP No. 312 (1987) shows that the compound BRL-34915 is effective for the medical treatment of incontinence and pain.

WO8800-822-A (Patent Kohyo Koho No. Hei 2-500272) discloses that the compound BRL-34915 is useful for the hair-growth.

However, EP-A-28449 and EP-A-28064 show that the benzopyran derivatives to which the BRL-34915 belongs may undesirably affect the action of the heart.

As the result of the intensive research of novel compounds, therefore, the present inventors have found out that the novel pyranobenzoxadiazole derivatives have strong activity for lowering blood pressure. Then, the present inventors have accomplished the present invention.

SUMMARY OF THE INVENTION

The object of the present invention is to provide novel pyranobenzoxadiazole derivatives.

Another object of the present invention is to provide processes for producing the derivatives.

Still another object of the present invention is to provide methods for treating hypertension, cardiovascular disorder, cerebrovascular disorder and asthma and for hair-growth stimulation.

DETAILED DESCRIPTION OF THE INVENTION

The novel compounds of the present invention are represented by the formula (I):

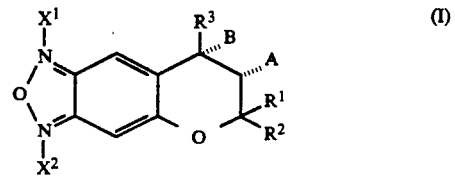

wherein $X^1$ and $X^2$ do not exist or represent oxygen atom;

A represents OH or acyloxy group having 1 to 4 carbon atoms;

B represents hydrogen atom;

A and B together represent a bond;

$R^1$ and $R^2$ are same or different from each other and represent hydrogen atom or alkyl group having 1 to 4 carbon atoms, or $R^1$ and $R^2$ together represent 1,2-ethylene, 1,3-propylene or 1,4-butylene, 1,5-pentylene, and these alkylene group may be substituted by alkyl group having 1 to 4 atoms;

$R^3$ represents cyclic amido group of the formula:

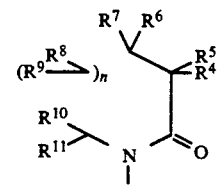

wherein n represents 0 or 1 and $R^4$, $R^5$, $R^6$, $R^7$, $R^8$, $R^9$, $R^{10}$ and $R^{11}$ represent hydrogen atom, alkyl group having 1 to 4 carbon atoms, halogen atom, $ONO_2$, $OSO_3H$, OH, acyloxy group having 1 to 4 carbon atoms, alkoxy group having 1 to 4 carbon atoms, tri-($C_1$-$C_4$ alkyl)-silyloxy group, diphenyl-$C_1$-$C_4$ alkyl)-silyloxy group, di-($C_1$-$C_4$ alkyl)-phenyl silyloxy group or

wherein $R^{12}$ and $R^{13}$ represent hydrogen atom, alkyl group having 1 to 4 carbon atoms or acyl group having 1 to 4 carbon atoms, or $R^{12}$ and $R^{13}$ together represent 5 or 6-membered cyclic amine which may be substituted by one or more than one alkyl group having 1 to 4 carbon atoms, or when n is 1, $R^5$ and $R^6$, $R^7$ and $R^8$ or $R^9$ and $R^{10}$ together represent a bond, or when n is 0, $R^5$ and $R^6$ or $R^7$ and $R^{10}$ together represent a bond, or $R^4$ and $R^5$, $R^6$ and $R^7$, $R^8$ and $R^9$ or $R^{10}$ and $R^{11}$ together represent=O, and the pharmacological acceptable salts of the compounds which can form salts have strong activity for lowering blood pressure.

EP-A-327127 (U.S. Pat. No. 4,900,752) discloses that pyranobezoxadiazol derivatives have an activity for lowering blood pressure. However, said EP-A-327127 does not refer to groups of compounds in which substituents at cyclic amido moiety are introduced.

The present inventors have introduced substituents at the cyclic amido moiety of pyranobenzoxadiazol derivatives and have studied influences affecting living activities. As a result, they have found out that the pyranobenzoxiadiazol derivatives which are introduced with substituents at the cyclic amido moiety thereof not only show very strong activity for lowering blood pressure, but also have remarkably continuous activity, resulting in accomplishing the present invention.

Although stereoisomer or optical isomer is contained in the compounds of the formula (I), the present invention contains all of these isomers.

Next, each substituent shown in the formula (I) is concretely explained.

In the reference examples and the synthesis examples of the present invention, the signal of "n-", "i-", "sec-", "t-" and "c-" represent "normal-", "iso-", "secondary-", "tertiary-" and "cyclo-", respectively.

Moreover, "Me" represents methyl group, "Et" does ethyl group, "Pr" does propyl group, "Bu" does butyl group, "Pent" does pentyl group, "Hex" does hexyl group and "Ph" does phenyl group.

Examples of alkyl group having 1 to 4 carbon atoms as $R^1$, $R^2$, $R^4$, $R^5$, $R^6$, $R^7$, $R^8$, $R^9$, $R^{10}$, $R^{11}$, $R^{12}$ and $R^{13}$ are methyl group, ethyl group, propyl group, i-propyl group, n-butyl group, i-butyl group, sec-butyl group and t-butyl group.

1, 2-ethylene, 1, 3-propylene, 1, 4-butylene or 1, 5-pentylene formed by $R^1$ and $R^2$ which may be substituted by alkyl group having 1 to 4 carbon atoms can be $(CH_2)_2$, $(CH_2)_3$, $(CH_2)_4$ and $(CH_2)_5$.

Examples of acyloxyl group of A, $R^4$, $R^5$, $R^6$, $R^7$, $R^8$, $R^9$, $R^{10}$ and $R^{11}$ are OC(O)Me, OC(O)Et, OC(O)-n-Pr, OC(O)-i-Pr, OC(O)-n-Bu, OC(O)-i-Bu, OC(O)-sec-Bu, OC(O)-t-Bu may be used.

There may be a case that A and B together represent a bond.

The substituents of $R^4$, $R^5$, $R^6$, $R^7$, $R^8$, $R^9$, $R^{10}$ and $R^{11}$ are explained below.

Examples of halogen atom are fluorine atom, chlorine atom, bromine atom and iodine atom.

Alkoxy group having 1 to 4 carbon atoms is methoxy group, ethoxy group, n-propoxy group, i-propoxy group, n-butoxy group, i-butoxy group, sec-butoxy group and t-butoxy group may be used.

Tri-($C_1$–$C_4$ alkyl)-silyloxy group is trimethyl silyloxy group and t-butyldimethyl silyloxy group.

Diphenyl-($C_1$–$C_4$ alkyl)-silyloxy group is t-butyldiphenyloxy group.

Di-($C_1$–$C_4$ alkyl)-phenylsilyloxy group is phenyldimethyl silyloxy.

Examples of acyl group having 1 to 4 carbon atoms of $R^{12}$ and $R^{13}$ are C(O)Me, C(O)Et, C(O)-n-Pr, C(O)-i-Pr, C(O)-n-Bu, C(O)-i-Bu, C(O)-sec-Bu and C(O)-t-Bu.

Examples of cyclic amine formed by $R^{12}$ and $R^{13}$ are pyrrolidine, piperidine, morphorine and piperazine which may be substituted by one or more than one alkyl group having 1 to 4 carbon atoms.

Now, the process for producing the compounds according to the present invention is explained.

Amine of the formula (II) and lactone of the formula (III) are reacted without solvent or in an inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, and if necessary, in the presence of dimethylaluminum chloride ($Me_2AlCl$) or phosphorus oxychloride ($POCl_3$), at $-70°$ C. to $200°$ C., preferably, $-10°$ C. to $180°$ C. to obtain alcohol derivative of the formula (IV).

The obtained alcohol derivative of the formula (IV) is reacted with suitable halogenating agent such as triphenylphosphine-carbontetrachloride, triphenylphosphinecarbontetrabromide, iodide-triphenylphosphine, thionylchloride, thionylbromide, phosphorous oxychloride and phosphorous pentachloride, in an inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, at $-70°$ C. to $200°$ C., preferably, at $-10°$ C. to $60°$ C. to substitute alcohol group in the compound to halogen or convert alcohol into sulphonate by reacting the alcohol with sulfonylchloride such as methanesulfonyl chloride (MsCl) and paratoluensulfonyl chloride (TsCl) in an inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, in the presence of suitable base such as triethylamine, diisopropylethyl amine, pyridine, imidazol, at $-70°$ C. to $200°$ C., preferably, $-10°$ C. to $60°$ C. to be lead into the compound of the formula (V) in which Y represents Cl, Br, I, paratoluenesulfonyl group (OTs) or methanesulfonyl group (OMs). The compound of the formula (V) may be lead into cyclic amide of the formula (VI) by being reacted in suitable inert solvent such as acetone, dimethylformamide, dimethylacetamide, dimethylsufoxide, in the presence of suitable base such as potassium carbonate, sodium hydroxide, potassium hydroxide, quaternary ammonium hydroxide such as $Me_4NOH$, $Et_4NOH$, n-$Pr_4NOH$, $PhCH_2Me_3NOH$, at $-70°$ C. to $200°$ C., preferably, $-10°$ C. to $60°$ C. In the formula (VI), $X^1$, $X^2$, $R^1$, $R^2$, $R^4$, $R^5$, $R^6$, $R^7$, $R^8$, $R^9$, $R^{10}$, $R^{11}$ and n have the same meanings defined above.

The compounds of the formula (VI) may be readily dehydrated in an inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, in the presence of suitable base such as NaH, KH, 1,8-diazabicyclo[5,4,0]-7-undesen(DBU), potassium carbonate, sodium carbonate, potassium hydroxide, sodium hydroxide, at $-70°$ C. to $200°$ C., preferably $-10°$ C. to $60°$ C. to obtain the compounds of the formula (VII).

Among the compounds of the formula (I), compounds in which A presents acyloxy group may be obtained by reacting hydroxy group of the compound of the formula (VI) with acylhalide such as acetyl chloride, acetyl bromide, propionyl chloride, propionyl bromide, butyl chloride, butyryl bromide, isobutyryl chloride, isobutyryl bromide, valeryl chloride, valeryl bromide, in the presence of suitable base such as triethylamine, diisopropylethylamine, pyridine, imidazole, in suitable inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, at $-70°$ C. to $200°$ C., preferably $-10°$ C. to $60°$ C.

Intermediate compounds represented by the formula (V) may be also synthesized by the following method.

Namely, amines of the formula (II) are reacted with carboxylic acids of the formula (VIII) in the presence of suitable condensing agent such as dichlohexylcarbodiimide (DCC) in an inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, at −70° C. to 200° C., preferably −10° C. to 60° C. to obtain the compounds of the formula (V).

The amines of the formula (II) are reacted with the compounds of the formula (IX) in which Z represents halogen atom such as Cl, Br or I or

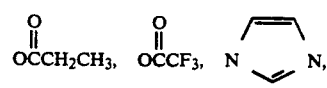

if necessary, in the presence of suitable base such as triethylamine, diisopropylethylamine, prydine and imidazole, in suitable inert solvent such as benzene, toluene, xylene, diethylether, diisopropylether, tetrahydrofuran, chloroform, dichloromethane, dichloroethane, dimethylformamide, dimethylacetamide, dimethylsulfoxide or ethyl acetate, at −70° C. to 200° C., preferably −10° C. to 60° C. to be similarly lead into the compounds of the formula (V).

In the formulae of the following reaction scheme, $X^1$, $X^2$, $R^1$, $R^2$, $R^4$, $R^5$, $R^6$, $R^7$, $R^8$, $R^9$, $R^{10}$, $R^{11}$ and n have the same meanings defined in the formulae (I) and (V).

Reaction schemes

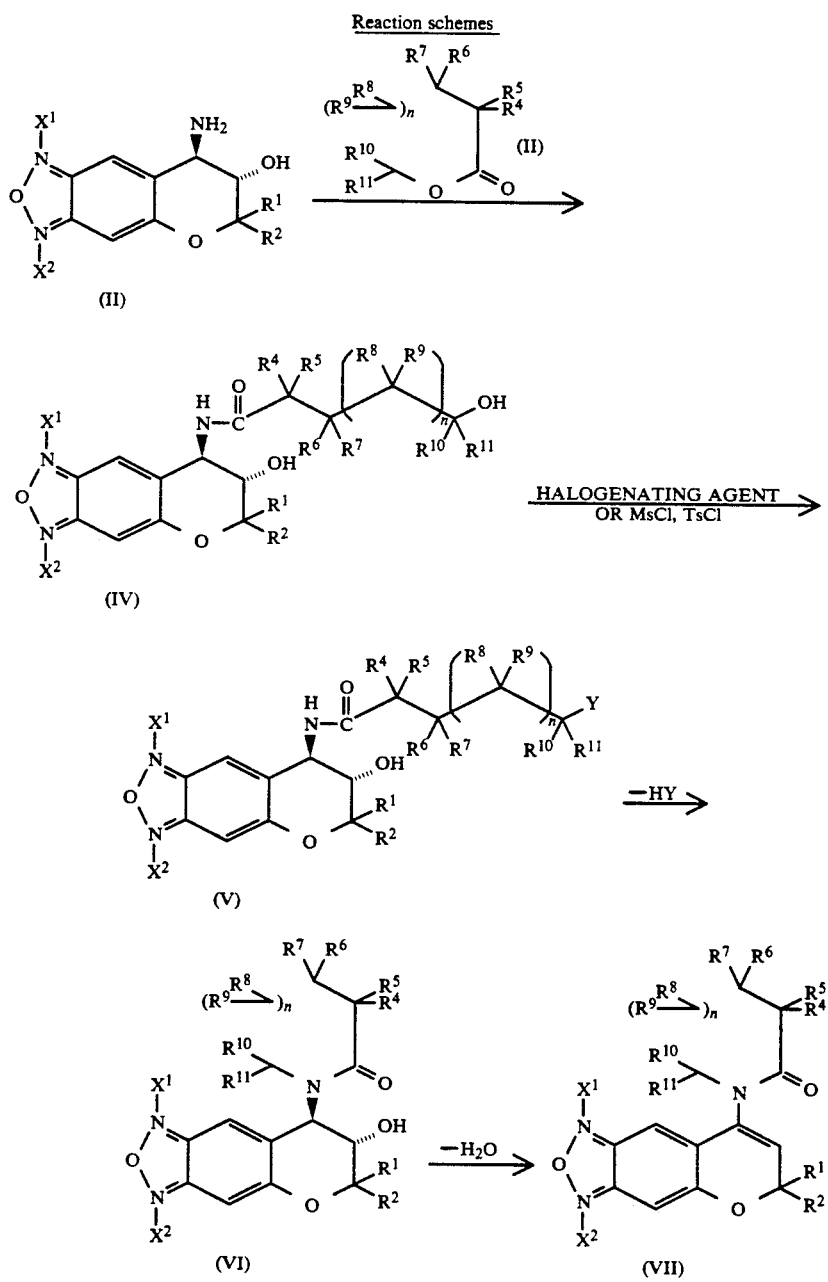

Reaction schemes

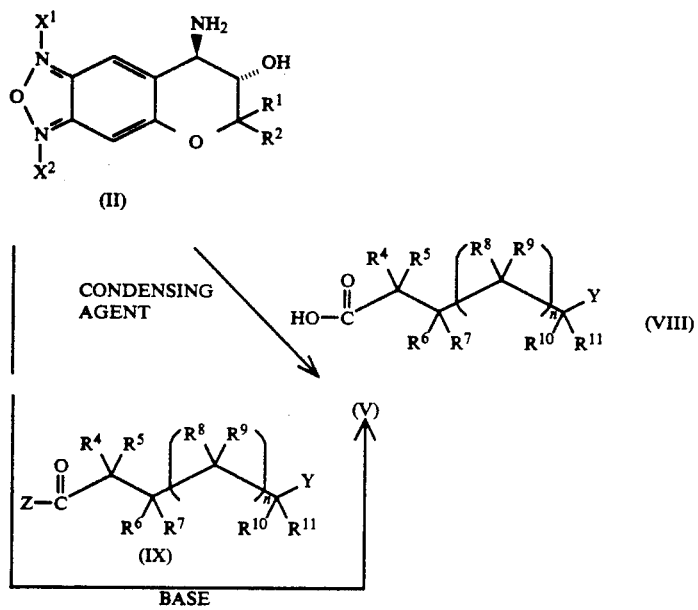

As described above, the present inventors have found out that the compounds of the present invention have strong vasolidating activity and activity for lowering blood pressure. Accordingly, the present compounds are considered to be useful as a medicament in the therapy of hypertension, angina pectoris, arrhythmia, cerebrovascular disorder and asthma of mammals inclusive of human being and hair-growth stimulants. Therefore, the present invention provides pharmaceutical compositions containing effective amount of the present compounds for the theraphy of the above-mentioned diseases.

As the manner of administration of the present compounds, there may be mentioned a parenteral administration by injection (subcutaneous, intravenous, intramuscular or intraperitoneal injection), an ointment, a suppository or an aerosol, or an oral administration in the form of tablets, capsules, granules, pills, sirups, liquids, emulsions or suspensions.

The above pharmacological or veterinary composition contains the present compounds in an amount of from about 0.01 to 99.5% by weight, preferably from about 0.1 to 30% by weight, based on the total weight of the composition.

To the present compounds or to the compositions containing the present compounds, other pharmacologically or veterinarily active compounds may be incorporated. Further, the composition of the present invention may contain a plurality of the present compounds.

The clinical dose of the present compounds varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The present compounds may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as hydroxypropyl cellulose, sirups, gum arabic, gelatin, sorbitol, tragacanth gum, methyl cellulose or polyvinylpyrrolidone; a disintegrant such as starch, carboxymethyl cellulose or its calcium salt, crystal cellulose powder or polyethylene glycol; a lubricant such as talc, magnesium or calcium stearate, colloidal silica, sodium laurate or glycerol.

The injections, solutions, emulsions, suspensions, sirups or aerosols, may be prepared by using a solvent for the active ingredient such as water, ethyl alcohol, isopropyl alcohol, propylene glycol, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacanth gum or gum arabic; or a preservative such as a paraoxy benzoic acid, benzalkonium chloride or a salt of sorbic acid. Likewise, ointments may be prepared by using, e.g., white vaseline, liquid paraffin, a higher alcohol, Macrogol ointment, hydrophilic ointment or hydrogel base. The suppositories may be prepared by using, e.g., cocoa butter, polyethylene glycol, lanolin, fatty acid triglyceride, coconut oil or polysorbate.

Examples

Now, the present invention is explained referring to examples, but it is not to be limited by these examples.

(Test Examples) Antihypertensive effect

The present compounds were dissolved or suspended in the solvent (polyethylene glycol $400:H_2O=3:1$ (v/v)) and adminstered to three male spontaneously hypertensive rats (SHR, 11 weeks) via an oral route.

Systolic blood pressure (SBP) was measured by a tailcuff method (Natsume Seisakusho Co., Ltd., KN-210-1) at p.o. (per oral) administration of the compounds. SHR were prewarmed at 50° C. for 3 to 5 min.

in a warm box and placed into a restraining cage on heating plate (37° C.) for 5 to 15 min.

Table shows the % decrease of systolic blood pressure at one hour, 3 hours and 5 hours after administration of the test compounds. Each value represents the mean of three animals. (*: polyethylene glycol of molecular weight range 380–420)

TABLE

| Test Compound | Dosage (mg/kg) | Ratio of lowering blood pressure (%) | | |
|---|---|---|---|---|
| | | 1 h. | 3 h. | 5 h. |
| Compound B4 | 0.1 | 29 | 22 | 17 |
| Compound B10 | 0.3 | 28 | 14 | 8 |
| Compound of Example 5 | 0.1 | 24 | 12 | 13 |
| Compound of Example 17 | 0.3 | 35 | 26 | 17 |
| BRL-34915 | 0.3 | 27 | 4 | 5 |

Reference Example 1

7,8-dihydro-6,6-dimethyl-7-hydroxy-8-(n-(1-oxo-3-t-butyldimethylsilyloxy-5-hydroxy)pentyl)amino-6H-pyrano[2,3-f]benzo-2,1,3-oxadiazole To 810 mg of (±)β-t-butyldimethylsilyloxy-δ-valerolactone were added 800 mg of (+)-7,8-dihydro-6,6-dimethyl- 7-hydroxy-8-amino-6H-pyrano[2,3-f]benzo-2,1,3-oxadiazol and heated at 100° C. for 3 hours. The reaction mixture was subjected to a silica gel column chromatography (ethyl acetate) to obtain 600 mg (38%) cf the intended compound having low polarity as colorless oily solid (Compound A1) and obtain 430 mg (27%) of the intended compound having high polarity as colorless crystals (diastereomer of the Compound A1; Compound B).

m.p. 94.0° C.-96.0° C.

Reference Example 2

7,8-dihydro-6,6-dimethyl-7-hydroxy-8-(n-(1-oxo-3-t-butyldimethylsilyloxy-5-bromo)pentyl)amino-6H-pyrano[2,3-f ]benzo-2,1,3-oxadiazole To 570 mg of the compound A1 dissolved in 10 mL of diethylether were added 650 mg of triphenylphosphine, 820 mg of carbontetrabromide and 250 mg of pyridine and reacted at 30° C. to 40° C. for one and half hours. After cooling, the precipitate was separated by filtration and the solvent was distilled off under reduced pressure. The residue was subjected to a silica gel column chromatography (ethyl acetate:n-hexane=1:1, Rf=0.6) to obtain 420 mg (65%) of the intended compound (Compound A2) as pale yellow oil.

In the similar process, 390 mg (65%) of the intended compound (diastereomer of the compound A2; Compound B2) was obtained from 530 mg of the compound B1, as yellow oil.

Synthesis Example 1

7,8-dihydro-6,6-dimethyl-7-hydroxy-8-(2-oxo-4-t-butyl-dimethylsilyloxy-1-piperidinyl)-6H-pyrano[2,3-f]benzo-2,1,3-oxadiazole (Compound A3)

To 400 mg of the compound A2 dissolved in 23 g of dimethylformamide was dropwise added a solution of 1.2 g of 10% aqueous solution of tetraethylammonium hydroxide and 12 g of anhydrous dimethylsulfoxide over 30 min. After the mixture was reacted at the room temperature for 30 min., the mixture was added with 50 mL of saturated aqueous ammonium chloride solution and 50 mL of saturated aqueous NaCl solution and extracted with 50 mL of ethyl acetate. After the solvent was distilled off under reduced pressure, the residue was subjected to a silica gel column chromatography (ethyl acetate:n-hexane=2:1, Rf=0.6) to obtain 230 mg (68%) of the intended compound (Compound A3) as colorless needle-shaped crystals.

m.p.: 219.0° C.-220.5° C.

Synthesis Example 2

7,8-dihydro-6,6-dimethyl-7-hydroxy-8-(2-oxo4-t-butyl-dimethylsilyloxy-1-piperidinyl)-6H-pyrano[2,3-f]benzo-2,1,3-oxadiazole (Compound B3)

In the similar process, 230 mg (73%) of the intended compound (diastereomer of the compound A3; Compound B3) was obtained from 370 mg of the compound B2, as yellow crystals.

m.p. 221.0° C.-223.0° C.

Synthesis Example 3

7,8-dihydro-6,6-dimethyl-7-hydroxy-8-(2-oxo-4-hydroxy-1-piperidinyl)-6H-pyrano[2,3-f]benzo-2,1,3-oxadiazole (Compound A4)

To 200 mg of the compound A3 dissolved in 5 mL of tetrahydrofuran was added 1 mL of 1 mol solution of tetra-n-butylammonium fluoride in tetrahydrofuran and reacted at the room temperature for one hour. After the solvent was distilled off under reduced pressure, the residue was subjected to a silica gel column chromatography (ethyl acetae:n-hexane=9:1, Rf=0.5) to obtain 120 mg (81%) of the intended compound (Compound A4) as colorless crystals.

m.p.: 200.0° C.-201.0° C.

Synthesis Example 4

7,8-dihydro-6,6-dimethyl-7-hydroxy-8-(2-oxo-4-hydroxy-1-piperidinyl)-6H-pyrano[2,3-f]benzo-2,1,3-oxadiazole (Compound B4)

In the similar process, 120 mg (81%) of the intended compound (diastereomer of the compound A4; Compound B4) were obtained as colorless crystals from 200 mg of the compound B3.

m.p.: 203.0° C.-206.0° C.

Synthesis Example 5

7,8-dihydro-6,6-dimethyl-7-hydroxy-8-(2,4-dioxo-1-piperidinyl)-6H-pyrano[2,3-f]benzo-2,1,3-oxadiazole 300 mg of the compound A4 dissolved in 30 mL of acetone were cooled to 0° C. and added with Jones reagent (J. Chem. Soc., 1946, 39) until the color of the mixed solution fell into unchange. After the obtained solution was stirred at 0° C. for 30 min., the mixture was added with 1 mL of i-propanol, followed by adding 20 mL of water and extracted with 50 mL of ethyl acetate and washed with 40 mL of 5% sodium hydrogencarbonate solution. After the solution was dried over anhydrous magnesium sulfate, the solvent was distilled off under reduced pressure. The residue was subjected to a slica gel column chromatography (ethyl acetate:n-hexane=1:1, Rf=0.10) to obtain 110 mg of the intended compound as colorless crystals.

m.p.: 220.0° C.-223.0° C.

Synthesis Example 6

7,8-dihydro-6,6-dimethyl-7-hydroxy-8-(4,4-dimethyl-2-oxo-1-piperidinyl)-6H-pyrano[2,3-f]benzo-2,1,3-oxadiazole To 654 mg of (+)-7,8-dihydro-6,6-dimethyl-7-hydroxy-8-amino-6H-pyrano[2,3-f]benzo-2,1,3-oxadiazole dissolved in 10 mL of ethyl acetate were added 337 mg of triethylamine and dropwise added 696 mg of 5-bromo-3,3-dimethylvaleryl chloride at the room temperature over a 10-minute period, followed by stirring at the room temperature for one hour. The reaction mixture was added with 20 ml of saturated aqueous NaCl solution, and extracted twice with ethyl acetate (each 20 mL). After the extract was dried over anhydrous sodium sulfate and the solvent was distilled off under reduced pressure. The residue was dissolved in 66 g of dimethylformamide and was dropwise added with 2.7 g of 20% tetraethylammonium hydroxide solution over 20 minutes under ice-cooling. Under ice-cooling, the mixture was reacted for 30 min. and then, the solvent was distilled off under reduced pressure and was added with 20 mL of saturated aqueous NaCl solution and extracted thrice with methylchloride (each 20 mL). After the extract was dried over anhydrous sodium sulfate, the solvent was distilled off under reduced pressure The residue was subjected to a silica gel column chromatography (ethyl acetate:n-hexane=1:1, Rf=0.5) to obtain 598 mg of the intended compound as colorless crystals.

m.p. 184.0° C.–187.0° C.

Reference Example 3

7,8-dihydro-6,6-dimethyl-7-hydroxy-8-(n-(1-oxo-3-t-butyldimethylsilyloxy-4-hydroxy)butyl)amino-6H-pyrano[2,3-f]benzo-2,1,3-oxadiazole To 12.39 g of (±)-β-t-butyldimethylsilyloxy-γ-butyrolactone were added 13.48 g of (+)-7,8-dihydro-6,6-dimethyl-7-hydroxy-8-amino-6H-pyrano[2,3-f]benzo-2,1,3-oxadiazole and heated at 100° C. for 23 hours. The reaction mixture was subjected to a silica gel column chromatography (ethyl acetate:n-hexane=1:1) to obtain 12.50 g (48%) of the intended compound (Compound A5) having low polarity as brown oil and 4.17 g (16%) of the intended compound (diastereomer of the compound A5; Compound B5) having high polarity as brown oil.

Synthesis Example 7

7,8-dihydro-6,6-dimethyl-7-hydroxy-8-(2-oxo-4-t-butyl-dimethylsilyloxy-1-pyrrolidinyl)-6H-pyrano[2,3-f]benzo-2,1,3-oxadiazole (Compound A7)

To 2.34 g of the compound A5 dissolved in 100 mL of absolute dichloromethane were added 1.09 g of p-toluensulfonylchloride under ice-cooling, followed by stirring at the room temperature for 16 hours. The reaction solution was diluted with 200 mL of dichloromethane and washed with 150 mL of water and then, dried over anhydrous sodium sulfate. After the solvent was distilled off under reduced pressure, the residue was subjected to a silica gel column chromatography (ethyl acetate:n-hexane=2:1, Rf=0.75) to obtain 1.19 g (53%) of the intended compound (Compound A7) as pale yellow oil.

Reference Example 4

7,8-dihydro-6,6-dimethyl-7-hydroxy-8-(n-(1-oxo-3-t-butyldimethylsilyloxy-4-bromo)butyl)amino-6H-pyrano[2,3-f]benzo-2,1,3-oxadiazole (Compound B6)

To 4.17 g of the compound B5 dissolved in 120 mL of diethyl ether were added 4.85 g of triphenylphosphine, 6.14 g of carbontetrabromide and 1.83 g of pyridine and stirred at the room temperature for 5 hours. The precipitate was filtered and the solvent was distilled off under reduced pressure. Thereafter, the residue was subjected to a silica gel column chromatography (ethyl acetate:n-hexane=1:1, Rf=0.5) to obtain 1.44 g (30%) of the intended compound (Compound B6) as pale yellow oil solid.

Synthesis Example 8

7,8-dihydro-6,6-dimethyl-7-hydroxy-8-(2-oxo-4-t-butyl-dimethylsilyloxy-1-pyrrolidinyl)-6H-pyrano[2,3-f]benzo-2,1,3-oxadiazole (Compound B7)

To 1.44 g of the compound B6 dissolved in 86 g of dimethylformamide were dropwise added 20% aqueous solution of tetramethylammonium hydroxide, followed by stirring at the room temperature for one hour. The mixture was, then, added with 30 mL of saturated aqueous ammonium chloride solution and 20 mL of saturated aqueous NaCl solution and extracted with 200 mL of ethyl acetate. The solvent was distilled off under reduced pressure to obtain 1.24 g of the intended compound (diastereomer of the compound A7; Compound B7) as pale yellow oil.

Synthesis Example 9

7,8-dihydro-6,6-dimethyl-7-hydroxy-8-(2-oxo-4-hydroxy-1-pyrrolidinyl)-6H-pyrano[2,3-f]benzo-2,1,3-oxadiazole (Compound A8)

To 1.18 g of the compound A7 dissolved in 30 mL of tetrahydrofuran were added 3.54 g of 1 mol solution of tetra-n-butylammonium fluoride in tetrahydrofuran and stirred at the room temperature for 2 hours. After the solvent was distilled off under reduced presssure, the residue was subjected to a silica gel column chromatography (ethyl acetate, Rf=0.3) to obtain 618 mg (71%) of the intended compound (Compound A8) as pale yellow crystals.

m.p.: 179.0° C.–183.0° C.

Synthesis Example 10

7,8-dihydro-6,6-dimethyl-7-hydroxy-8-(2-oxo-4-hydroxy-1-pyrrolidinyl)-6H-pyrano[2,3-f]benzo-2,1,3-oxadiazole (Compound B8)

In the similar process, 431 mg (48%) of the intended compound (diastereomer of the compound A8; Compound B8) were obtained as pale yellowish white crystals from 1.24 g of the compound B7.

m.p.: 238.0° C.–239.0° C.

Reference Example 5

7,8-dihydro-6,6-dimethyl-7-hydroxy-8-(n-(1-oxo-2-t-butyldimethylsilyloxy-4-hydroxy)butyl)amino-6H-pyrano[2,3-f]benzo-2,1,3-oxadiazole To 4.00 g of (±)-β-t-butyldimethylsilyloxy-γ-butyrolactone were added 13.48 g of (+)-7,8-dihydro-6,6-dimethyl-7-hydroxy-8-amino-6H-pyrano[2,3-f]benzo-2,1,3-oxadiazole and heated at 100° C. for 23 hours. The reaction mixture was subjected to a silica gel column chromatography (ethyl acetate:n-hexane=1:1) to obtain 5.67 g of the intended compound (mixture of diastereomer) as brown oil.

Reference Example 6

7,8-dihydro-6,6-dimethyl-7-hydroxy-8-(n-(1-oxo-2-t-butyldimethylsilyloxy-4-iodo)butyl)amino-6H-pyrano[2,3-f]benzo-2,1,3-oxadiazole To 2.69 g of triphenylphosphine dissolved in 25 mL of absolute dichloromethane were added 3.86 g of the compound synthesized by the Reference Example 5 and 0.68 g of imidazole and added 2.39 g of iodine, followed by stirring at the room temperature for 2 hours. After the reaction solution was added with 3.4 mL (6.6%) of aqueous sodium thiosulfate solution, the mixture was extractd with 10 mL of dichloromethane and washed with 30 mL of saturated aqueous NaCl solution and then, dried over anhydrous magnesium sulfate. After the solvent was distilled off under reduced pressure, the residue was subjected to a silica gel column chromatography (ethyl acetate:n-hexane=2:1, Rf=0.8) to obtain 3.35 g (70%) of the intended compound (mixture of diastereomer) as pale yellow oil.

Synthesis Example 11

7,8-dihydro-6,6-dimethyl-7-hydroxy-8-(2-oxo-3-t-butyl-dimethylsilyloxy-1-pyrrolidinyl)-6H-pyrano[2,3-f]benzo-2,1,3-oxadiazole 3.35 g of the compound synthesized by the Reference Example 6 was dissolved in 196 mL of dimethylformamide. To the mixture was dropped with 5.7 mL of 20% aqueous solution of tetramethylammonium hydroxide and stirred at the room temperature for one hour. Thereafter, the mixture was added with 70 mL of saturated ammonium chloride solution and 50 mL of saturated aqueous NaCl solution and extracted ith 500 mL of ethyl acetate. After the solvent was distilled off under reduced pressure, the residue was subjected to a silica gel column chromatography (ethyl acetate:n-hexane=2:1, Rf=0.45) to obtain 620 mg (24%) of the intended compound (mixture of diastereomer) as pale yellow oil.

Synthesis Example 12

7,8-dihydro-6,6-dimethyl-7-hydroxy-8-(2-oxo-3-hydroxy-1-pyrrolidinyl)-6H-pyrano[2,3-f]benzo-2,1,3-oxadiazole (Compounds A9 and B9)

To 510 mg of the compound synthesized by the Synthesis Example 11 dissolved in 13 mL of tetrahydrofuran were added 1.39 g of 1 mol solution of tetra-n-butylammonium fluoride in tetrahydrofuran , followed by stirring at the room temperature for one hour. After the solvent was distilled off under reduced pressure, the residue was subjected to a silica gel column chromatography (methanol:chloroform=1:5, Rf=0.55) to obtain 350 mg (92%) of the intended compound (mixture of diastereomer) as pale yellowish white crystals. Moreover, the mixture was subjected to a silica gel thin layer chromatography (methanol:chloroform=1:8) to obtain 178 mg of the intended compound (Compound A9) having low polarity (m.p.: 195.0 ° C.-196.0° C.) and to obtain 100 mg of the intended compound (diastereomer of the compound A9; Compound B9) having high polarity as pale yellow crystals.

m.p.: 243.0° C.-244.0° C.

Reference Example 7

7,8-dihydro-6,6-dimethyl-7-hydroxy-8-(n-(1-oxo-3-methyl-5-bromo)pentyl)amino-6H-pyrano[2,3-f]benzo-2,1,3-oxadiazole To 1.41 g of (+)-7,8-dihydro-6,6-dimethyl-7-hydroxy-8-amino-6H-pyrano[2,3-f]benzo-2,1,3-oxadiazole dissolved in 20 mL of ethyl acetate was added 1.0 g of tri-ethylamine. The mixture was dropwise added with 1.5 g of 5-bromo-3-methylvaleryl chloride at the room temperature over 15-minute period and reacted at the room temperature for one hour. The reaction mixture was added with 40 mL of saturated aqueous NaCl solution and extracted twice with ethyl acetate (each 40 mL). After the extract was dried over anhydrous sodium sulfate, the solvent was distilled off under reduced pressure. The residue was subjected to a silica gel column chromatography (ethyl acetate:n-hexane=2:1, Rf=0.6) to obtain 2.1 g of the intended compound as yellow oil.

Synthesis Example 13

7,8-dihydro-6,6-dimethyl-7-hydroxy-8-(2-oxo-4-methyl-1-piperidinyl)-6H-pyrano[2,3-f]benzo-2,1,3-oxadiazole To 1.0 g of the compound synthesized by the Reference Example 7 dissolved in 60 g of dimethylformamide were added a solution of 10% aqueous solution of tetraethylammonium hydroxide and 10 mL of dimethylsulfoxide under ice-cooling over 10-minute period. After the mixture was reacted at the room temperature for one hour, the solvent was distilled off under reduced pressure and then, added with 20 mL of water and extracted twice with ethyl acetate (each 20 mL). The residue was subjected to a silica gel column chromatography (ethyl acetate, Rf=0.6) to obtain 110 mg of the intended compound (Compound A10) having low porality as colorless crystals (m.p. 158.0° C.-159.0° C.) and 140 mg of the intended compound (diastereomer of the compound A10; Compound B10) having high polarity as pale yellow crystals.

Synthesis Example 14

7,8-dihydro-6,6-dimethyl-7-hydroxy-8-(2-oxo-4-acetoxy-1-piperidinyl)-6H-pyrano[2,3-f]benzo-2,1,3-oxadiazole To 100 mg of the compound A4 dissolved in 700 mg of absolute pyridine were added 50 mg of acetic anhydride. After the mixture was reacted at the room temperature over night, the reaction mixture was added with 20 mL of 5% hydrochloric acid and extracted twice with ethyl acetate (20 mL). After the extract was dried over anhydrous sodium sulfate, the solvent was distilled off under reduced pressure. The residue was subjected to a silica gel column chromatography (ethyl acetate:n-hexane=2:1) to obtain 30 mg of the intended compound as colorless crystals.

m.p. 204.0° C.-206.0° C.

Synthesis Example 15

7,8-dihydro-6,6-dimethyl-7-acetyl-8-(2-oxo-4-acetoxy-1-piperidinyl)-6H-pyrano[2,3-f]benzo-2,1,3-oxadiazole 60 mg of the intended compound as pale yellow oil were obtained by the similar operation with that of the Synthesis Example 14.

Synthesis Example 16

7,8-dihydro-6,6-dimethyl-7-hydroxy-8-(2-oxo-4-bromo-1-piperidinyl)-6H-pyrano[2,3-f]benzo-2,1,3-oxadiazole To 100 mg of the compound A4 dissolved in 3 mL of anhydrous tetrahydrofuran were added 160 mg of triphenylhosphine, 60 mg of absolute pyridine and 200 mg of carbontetrabromide, followed by stirring at the room temperature for one hour. After the solvent was distilled off under reduced presssure, the residue was subjected to a silica gel column chromatography (methanol:chloroform=20:1, Rf=0.4) to obtain 100 mg of the intended compound as pale yellowish white crystals.

m.p.: 250.0° C.-253.0° C.

Synthesis Example 17

7,8-dihydro-6,6-dimethyl-7-hydroxy-8-(2-oxo-piperidine-3-ene-1-yl)-6H-pyrano[2,3-f]benzo-2,1,3-oxadiazole To 30 mg of the compound obtained by the Synthesis Example 16 dissolved in 2 mL of anhydrous tetrahydrofuran were added 100 mg of DBU (1,8-diazabicyclo[5,4,0]undeca-7-ene) and reacted at the room temperature for one hour. The reaction mixture was added with 10 mL of 3% hydrochloric acid and extracted twice with chloroform (each 10 mL). After the extract was dried over anhydrous sodium sulfate, the solvent was distilled off under reduced pressure. The residue was added with diethylether and the precipitated crystals were filtered to obtain 20 mg of the intended compound as colorless crystals.

m.p.: 248.0° C.–250.0° C.

Synthesis Example 18

7,8-dihydro-6,6-dimethyl-7-hydroxy-8-(2-oxo-4-nitrooxy-1-piperidinyl)-6H-pyrano[2,3-f]benzo-2,1,3-oxadiazole (Compound A11)

To a solution of 60 mg of fuming sulfuric acid and 600 mg of acetic anhydride was added 100 mg of the compound A4 and reacted at the room temperature for 10 minutes. After the reaction mixture was added with 20 mL of water and stirred, the mixture was extracted with 30 mL of chloroform and the organic layer was washed with saturated sodium carbonate solution. After the organic layer was dried over anhydrous sodium sulfate, the solvent was distilled off under reduced pressure. The residue was subjected to a silica gel thin layer chromatography (ethyl acetate:n-hexane=1:1, Rf=0.5) to obtain 40 mg of the intended compound as colorless crystals.

m.p.: 204.0° C.–206.0° C.

Synthesis Example 19

7,8-dihydro-6,6-dimethyl-7-hydroxy-8-(2-oxo-4-nitrooxy-1-piperidinyl)-6H-pyrano[2,3-f]benzo-2,1,3-oxadiazole (Compound 11)

To a solution of 30 mg of fuming sulfuric acid and 600 mg of acetic anhydride was added 110 mg of the compound B4 under ice-cooling and reacted at the room temperature for 10 minutes. After the reaction mixture was added with 20 mL of water and stirred, the mixture was added with saturated aqueous sodium carbonate solution to be neutralized and extracted twice with 20 mL of chloroform. After the extract was dried over the anhydrous sodium carbonate, the solvent was distilled off under reduce pressure. The residue was added with diethyl ether and ethyl acetate and the precipitated crystals were filtered to obtain 110 mg of the intended compound (diastereomer of the compound A11; Compound B11) as pale yellow crystals.

m.p.: 186.0° C.–189.0° C.

Synthesis Example 20

7,8-dihydro-6,6-dimethyl-7-hydroxy-8-(2-oxo-3,3-dimethyl-1-piperidinyl)-6H-pyrano[2,3-f]benzo-2,1,3-oxadiazole To 289 mg of (+)-7,8-dihydro-6,6-dimethyl-7-hydroxy-8-amino-6H-pyrano[2,3-f]benzo-2,1,3-oxadiazole dissolved in 5 mL of ethyl acetate were added 149 mg of triethylamine. The mixture was dropwise added with 308 mg of 5-bromo-2,2-dimethylvaleryl chloride, followed by stirring at the room temperature for one and half hours. The mixture was added with 10 mL of saturated aqueous NaCl solution and twice extracted with ethyl acetate (each 20 mL). After the extract was dried over anhydrous sodium sulfate, the solvent was distilled off under reduced pressure. The residue was dissolved in 33 mL of dimethylformamide and was dropped with 1.24 g of 10% tetramethylammonium hydroxide solution under ice-cooling over 15-minute period. After the mixture was reacted under ice-cooling for one hour, the solvent was distilled off under reduced pressure and added with 10 mL of saturated aqueous NaCl solution and extracted twice with chloroform (each 20 mL). After the extract was dried over anhydrous sodium sulfate, the solvent was distilled off under reduced pressure. The residue was subjected to a silica gel column chromatography (ethyl acetate:n-hexane=1:1, Rf=0.5) to obtain 174 mg of the intended compound as fine yellow crystals.

m.p. 114.0° C.–115.0° C.

Reference Example 8

7,8-dihydro-6,6-dimethyl-7-hydroxy-8-(n-(1-oxo-4,4-dimethyl-5-bromo)pentyl)amino-6H-pyrano[2,3-f]benzo-2,1,3-oxadiazole To 583 mg of (+)-7,8-dihydro-6,6-dimethyl-7-hydroxy-8-amino-6H-pyrano[2,3-f]benzo-2,1,3-oxadiazole dissolved in 10 mL of ethyl acetate were added 301 mg of triethylamine. The mixture was dropwise added with 621 mg of 5-bromo-4,4-dimethylvaleryl chloride at the room temperature over 10 minutes, followed by stirring at the room temperature for one and half hours. The reaction mixture was added with 20 mL of saturated aqueous NaCl solution and extracted twice with ethyl acetate (20 mL). After the extract was dried over anhydrous sodium sulfate, the solvent was distilled off under reduced pressure. The residue was subjected to a silica gel column chromatography (ethyl acetate:n-hexane=1:2, Rf=0.2) to obtain 347 mg of the intended compound as yellow oil.

Synthesis Example 21

7,8-dihydro-6,6-dimethyl-7-hydroxy-8-(2-oxo-5,5-dimethyl-1-piperidinyl)-6H-pyrano[2,3-f]benzo-2,1,3-oxadiazole To 347 mg of the compound synthesized by the Reference Example 8 dissolved in 20 mL of dimethylformamide were dropwise added 742 mg of 10% aqueous tetramethylammonium hydroxide solution under ice-cooling for 15 min. After the mixture was reacted under ice-cooling for 30 min., the solvent was distilled off under reduced pressure, added with 15 mL of saturated aqueous NaCl solution and extracted twice with chloroform (20 mL). The residue was subjected to a silica gel column chromatography (ethyl acetate:n-hexane=2:1, Rf=0.4) to obtain 15.5 g of the intended compound as yellow crystals.

m.p.: 136.0° C.–137.0° C.

Reference Example 9

7,8-dihydro-6,6-dimethyl-7-hydroxy-8-(n-(1-oxo-4-methyl-5-bromo)pentyl)amino-6H-pyrano[2,3-f]benzo-2,1,3-oxadiazole To 1.54 g of (+)-7,8-dihydro-6,6-dimethyl-7-hydroxy-8-amino-6H-pyrano[2,3-f]benzo-2,1,3-oxadiazole dissolved in 50 mL were added 795 mg of triethylamine. The mixture was dropwise added with 1.40 g of 5-bromo-4-methylvaleryl chloride and reacted at the room temperature for 50 min. The reaction mixture was added with 50 mL of saturated aqueous NaCl solution and extracted twice with ethyl acetate (each 80 mL). After the extract was dried over anhydrous sodium sulfate, the solvent was distilled off under reduced pressure. The residue was subjected to a silica gel column chromatography (ethyl acetate:n-hexane=1:1, Rf=0.5) to obtain 1.22 g of the intended compound as yellow oil.

Synthesis Example 32

7,8-dihydro-6,6-dimethyl-7-hydroxy-8-(2-oxo-5-methyl-1-piperidinyl)-6H-pyrano[2,3-f]benzo-2,1,3-oxadiazole To 1.22 g of the compound synthesized by the Reference Example 9 dissolved in 75 mL of dimethylformamide were dropped with 2.82 g of 10% aqueous tetramethylammonium hydroxide solution under ice-cooling for 20 min. After the mixture was reacted under ice-cooling for 30 min., the solvent was distilled off under reduced pressure, added with 50 mL of saturated aqueous NaCl solution and extracted twice with chloroform (each 100 mL). After the extract was dried over anhydrous sodium sulfate, the solvent was distilled off under reduced pressure. The residue was subjected to a silica gel column chromatography (ethyl acetate:n-hexane=2:1, Rf=0.2) to obtain 500 mg of the intended compound as mixture of diastereomer.

Reference Example 10

7,8-dihydro-6,6-dimethyl-7-hydroxy-8-(n-(1-oxo-2-methyl-5-bromo)pentyl)amino-6H-pyrano[2,3-f]benzo-2,1,3-oxadiazole To 2.05 g of (+)-7,8-dihydro-6,6-dimethyl-7-hydroxy-8-amino-6H-pyrano[2,3-f]benzo-2,1,3-oxadiazole dissolved in 50 mL of ethyl acetate were added 1.06 g of triethylamine. The mixture was dropwise added with 1.87 g of 5-bromo-2-methylvaleryl chloride and reacted at the room temperature for 30 min. The reaction mixture was added with 80 mL of saturated aqueous NaCl solution and extracted twice with ethyl acetate (each 100 mL). After the extract was dried over anhydrous sodium sulfate, the solvent was distilled off under reduced pressure. The residue was subjected to a silica gel column chromatography (ethyl acetate:n-hexane=1:1) to obtain 436 mg of the intended compound (Compound A12) having low polarity as yellow oil and to obtain 439 mg of the intended compound (diastereomer of Compound A12; Compound B12) having high polarity as yellow oil.

Synthesis Example 23

7,8-dihydro-6,6-dimethyl-7-hydroxy-8-(2-oxo-3-methyl-1-piperidinyl)-6H-pyrano[2,3-f]benzo-2,1,3-oxadiazole (Compound A13)

To 436 mg of the Compound A12 dissolved in 30 mL of dimethylformamide were dropped with 1.01 g of 10% aqueous tetramethylammonium hydroxide solution under ice-cooling over 10-minute period. After the mixture was reacted under ice-cooling for 30 min., the solvent was distilled off under reduced pressure, added with 20 mL of saturated aqueous NaCl solution and extracted twice with chloroform (each 40 mL). After the extract was dried over anhydrous sodium sulfate, the solvent was distilled off under reduced pressure. The residue was subjected to a silica gel column chromatography (ethyl acetate:n-hexane=2:1, Rf=0.4) to obtain 117.2 mg of the intended compound (Compound A13) as pale yellow crystals.

m.p.: 157.0° C.–158.0° C.

Synthesis Example 24

7,8-dihydro-6,6-dimethyl-7-hydroxy-8-(2-oxo-3-methyl-1-piperidinyl)-6H-pyrano[2,3-f]benzo-2,1,3-oxadiazole (Compound B13)

To 439 mg of the Compound B12 dissolved in 30 mL of dimethylformamide were dropwise added with 1.02 g of 10% aqueous tetramethylammonium hydroxide solution under ice-cooling over 15-minute period. After the mixture was reacted under ice-cooling for 40 min., the solvent was distilled off under reduced pressure, added with 20 mL of saturated aqueous NaCl solution and extracted twice with chloroform (each 40 mL). After the extract was dried over anhydrous sodium sulfate, the solvent was distilled off under reduced pressure. The residue was subjected to a silica gel column chromatography (ethyl acetate:n-hexane=2:1, Rf=0.4) to obtain 55.5 mg of the intended compound (diastereomer of Compound A13; Compound B13) as pale yellow crystals.

m.p. 146.0° C.–149.0° C.

Reference Example 11

7,8-dihydro-6,6-dimethyl-7-hydroxy-8-(n-(1-oxo-4-(R)-hydroxy-5-t-butyldimethylsilyloxy)pentyl)amino-6H-pyrano[2,3-f]benzo-2,1,3-oxadiazole 2.69 g of (±)-7,8-dihydro-6,6-dimethyl-7-hydroxy-8-amino-6H-pyrano[2,3-f]benzo-2,1,3-oxadiazole were added to 2.66 g of (R)-4-t-butyldimethylsilyloxymethyl-γ-butyrolactone and heated at 100° C. for 46 hours. The reaction mixture was subjected to a silica gel column chromatography (chloroform:ethyl acetate=2:1) to obtain 2.3 g of the intended compound as pale yellow crystals of diastereomer mixture.

m.p.: 105.0° C.–109.0° C.

Reference Example 12

7,8-dihydro-6,6-dimethyl-7-hydroxy-8-(n-(1-oxo-4-(R)-2-methoxyethoxymethyloxy)-5-t-butyldimethylsilyloxy)-pentyl)amino-6H-pyrano[2,3-f]benzo-2,1,3-oxadiazole To 2.19 g of the compound synthesized by the Reference Example 9 dissolved in 20 mL of methylene chloride were added 2.43 g of diisopropylethylamine and 1.21 g of 2-methoxyethoxymethyl chloride and reacted at the room temperature for 2 days. The reaction mixture was added with 50 mL of 0.1 N hydrochloric acid and extracted with 150 mL of methylene chloride. After the solvent was distilled off under reduced pressure, the residue was subjected to a silica gel column chromatography (chloroform:ethyl acetate=3:1) to obtain 0.78 g (30%) of the intended compound (Compound A14) having low porality as pale yellow and 1.32 g (50%) of the intended compound (diastereomer of the compound A14; Compound B14) having high polarity as pale yellow oil.

Reference Example 13

7,8-dihydro-6,6-dimethyl-7-hydroxy-8-(n-(1-oxo-4-(R)-(2-methoxyethoxymethyloxy)-5-hydroxy)pentyl)amino-6H-pyrano[2,3-f]benzo-2,1,3-oxadiazole To 0.78 g of the compound A14 dissolved in 5 mL of tetrahydrofuran were added 1.6 mL of 1 mol solution of tetra-n-butylammonium fluoride in tetrahydrofuran and reacted at the room temperature for 7 hours. The reaction mixture was added with 30 mL of saturated aqueous NaCl solution and extracted with 100 ml of ethyl acetate. After the solvent was distilled off under reduced pressure, the residue was subjected to a silica gel column chromatography (ethyl acetate) to obtain 0.41 g (67%) of the intended compound (Compound A15) as pale yellow oil.

In the similar process, 0.84 g (81%) of the intended compound (diastereomer of the compound A15; Compound B15) from 1.32 g of the compound B14, as pale yellow oil.

Reference Example 14

7,8-dihydro-6,6-dimethyl-7-hydroxy-8-(n-(1-oxo-4-(R)-(2-methoxyethoxymethyloxy)-5-bromo)pentyl-)amino-6H-pyrano[2,3-f]benzo-2,1,3-oxadiazole To 0.41 g of the compound A15 dissolved in 20 mL of diethylether were added 0.50 g of triphenylhosphine, 0.62 g of carbontetrabromide and 0.19 g of pyridine and reacted at the room temperature for three and half hours. The precipitate was filtered off and the solvent was distilled off under reduced pressure. The residue was subjected to a silica gel column chromatography (chloroform:ethyl acetate=2:1, Rf=0.2) to obtain 0.23 g (49%) of the intended compound (Compound A16) as pale yellow oil.

In the similar process, 0.45 g (47%) of the intended compound (diastereomer of the compound A16; Compound B16) from 0.894 g of the compound B15, as pale yellow oil.

Synthesis Example 25

7,8-dihydro-6,6-dimethyl-7-hydroxy-8-(2-oxo-5-(R)-2-methoxyethoxymethyloxy)-1-piperidinyl)-6H-pyrano[2,3-f]benzo-2,1,3-oxadiazole (Compound A17)

To 235 mg of the compound A16 dissolved in 20 mL of dimethylformamide were added with a solution prepared by dissolving 99 mg of tetramethylammonium hydroxide-hydrate in 0.1 mL of water and reacted at the room temperature for 50 minutes. The reaction mixture was added with two drops of acetic acid and the solvent was distilled off under reduced pressure. The residue was added with 50 mL of saturated aqueous NaCl solution and extracted with 100 mL of ethyl acetate. After the solvent was distilled off under reduced pressure, the residue was subjected to a silica gel column chromatography (ethyl acetate, Rf=0.6) to obtain 88 mg (44%) of the intended compound (Compound A17) as colorless oil.

Synthesis Example 26

7,8-dihydro-6,6-dimethyl-7-hydroxy-8-(2-oxo-5-(R)-(2-methoxyethoxymethyloxy)-1-piperidinyl)-6H-pyrano[2,3-f]benzo-2,1,3-oxadiazole (Compound B17)

In the similar process, 0.15 g (41%) of the intended compound (diastereomer of the compound A17; Compound B17) was obtained from 0.45 g of the compound B16, as colorless oil.

Synthesis Example 27

7,8-dihydro-6,6-dimethyl-7-hydroxy-8-(2-oxo-5-(R)-hydroxy-1-piperidinyl)-6H-pyrano[2,3-f]benzo-2,1,3-oxadiazole (Compound A18)

To 81 mg of the compound A17 dissolved in 3 mL of methylene chloride was added 0.21 mL of borontrifluoride ethylate under ice-cooling and reacted at the room temperature for 3 hours. The reaction mixture was added with 10 mL of 5% aqueous sodium hydrogencarbonate solution and extracted with 50 mL of ethyl acetate. After the solvent was distilled off under reduced pressure, the residue was subjected to a silica gel column chromatography (chloroform:ethyl acetate=10:1, Rf=0.3) to obtain 17 mg (26%) of the intended compound (Compound A18) as colorless crystals.

m.p. 193.0° C.–198.0° C.

Synthesis Example 28

7,8-dihydro-6,6-dimethyl-7-hydroxy-8-(2-oxo-5-(R)-hydroxy-1-piperidinyl)-6H-pyrano[2,3-f]benzo-2,1,3-oxadiazole (Compound B18)

To 155 mg of the compound B17 dissolved in 2 mL of methylene chloride was added 500 mg of zinc bromide and reacted at the room temperature for one day. The reaction mixture was added with 100 mL of 5% aqueous sodium hydrogencarbonate solution and extracted with 50 mL of ethyl acetate. After the solvent was distilled off under reduced pressure, the residue was subjected to a silica gel column chromatography (chloroform:ethyl acetate=10:1, Rf=0.2) to obtain 16 mg (13%) of the intended compound (diastereomer of Compound A18; Compound B18) as colorless crystals.

m.p.: 178.0° C.–182.0° C.

Reference Example 15

7,8-dihydro-6,6-dimethyl-7-hydroxy-8-(n-(1-oxo-4-(S)-hydroxy-5-t-butyldimethylsilyloxy)-pentyl)amino-6H-pyrano[2,3-f]benzo-2,1,3-oxadiazole To 1.58 g of (±)-7,8-dihydro-6,6-dimethyl-7-hydroxy-8-amino-6H-pyrano[2,3-f]benzo-2,1,3-oxadiazole were added 2.32 g of (S)-4-t-butyldimethylsilyloxymethyl-γ-butyrolactone and heated at 100° C. for 28 hours. The reaction mixture was subjected to a silica gel column chromatography (chloroform:ethyl acetate=2:1, Rf=0.1) to obtain 1.68 g (54%) of the intended compound as mixture of diastereomer. (colorless oil)

Reference Example 16

7,8-dihydro-6,6-dimethyl-7-hydroxy-8-(n-(1-oxo-4-(S)-(2-methoxyethoxymethyloxy)-5-t-butyldimethylsilyloxy)-pentyl)amino-6H-pyrano[2,3-f]benzo-2,1,3-oxadiazole To 1.68 g of the compound synthesized by the Reference Example 15 dissolved in 20 mL of methylene chloride were added 3.63 g of diisopropylethylamine and 1.69 g of 2-methoxyethoxymethyl chloride and reacted at the room temperature for 8 days. The reaction mixture was added with 20 mL of 0.1 N hydrochloric acid and extraced with 100 mL of ethyl acetate. After the solvent was distilled off under reduced pressure, the residue was subjected to a silica sol column chromatography (chloroform:ethyl acetate=3:1) to obtain 0.87 g (43%) of the intended compound (Compound A19) having low porality as pale yellow oil and 0.77 g (38%) of the intended compound (diastereomer of the compound A19; Compound B19) having high polarity as pale yellow oil.

Reference Example 17

7,8-dihydro-6,6-dimethyl-7-hydroxy-8-(n-(1-oxo-4-(S)-(2-methoxyethoxymethyloxy)-5-hydroxy)pentyl-)amino-6H-pyrano[2,3-f]benzo-2,1,3-oxadiazole To 0.87 g of the compound A19 dissolved in 10 mL of tetrahydrofuran were added 1.75 mL of 1 mol solution of tetra-n-butylammonium fluoride in tetrahydrofuran and reacted at the room temperature for 4 hours. The reaction mixture was added with 50 mL of saturated aqueous NaCl solution and extraced with 150 mL of ethyl acetate. After the solvent was distilled off under reduced pressure, the residue was subjected to a silica gel column chromatography (ethyl acetate, Rf=0.1) to obtain 0.57 g (83%) of the intended compound (Compound A20) as pale yellow oil.

In the similar process, 0.43 g (71%) of the intended compound (diastereomer of the compound A20; Compound B20) as pale yellow oil was obtained from 0.77 g of the compound B19.

Reference Example 18

7,8-dihydro-6,6-dimethyl-7-hydroxy-8-(n-(1-oxo-4-(S)-(2-methoxyethoxymethyloxy)-5-bromo)pentyl-)amino-6H-pyrano[2,3-f]benzo-2,1,3-oxadiazole To 0.57 g of the compound A20 dissolved in a mixture solution of 10 mL of diethylether and 10 mL of methylene chloride were added 0.69 g of triphenylphosphine, 0.94 g of carbontetrabromide and 0.3 mL of pyridine and reacted at the room temperature for 4 hours. The precipitate was filtered off and the solvent was distilled off under reduced pressure. The residue was subjected to a silica gel column chromatography (chloroform:ethyl acetate=2:1, Rf=0.2) to obtain 0.36 g (56%) of the intended compound (Compound A21) as pale yellow oil.

In the similar process, 0.27 g (54%) of the intended compound (diastereomer of the compound A21; Compound B21) as pale yellow oil.

Synthesis Example 29

7,8-dihydro-6,6-dimethyl-7-hydroxy-8-(2-oxo-5-(S)-(2-methoxyethoxymethyloxy)-1-piperidinyl)-6H-pyrano[2,3-f]benzo-2,1,3-oxadiazole (Compound A22)

To 360 mg of the compound A21 dissolved in 30 mL of dimethylformamide was added a solution prepared by dissolving 155 mg of tetramethylammonium hydroxide-hydrate in 0.15 mL of water and reacted at the room temperature for one hour. The reaction mixture was added with two drops of acetic acid and the solvent was distilled off under reduced pressure. The residue was added with 50 mL of saturated aqueous NaCl solution and extracted with 100 mL of ethyl acetate. After the solvent was distilled off under reduced pressure, the residue was subjected to a silica gel column chromatography (chloroform:ethyl acetate=2:1, Rf =0.1) to obtain 66 mg (21%) of the intended compound (Compound A22) as colorless oil.

| Formulation Example 1 | |
|---|---|
| Tablets | |
| Compound B4 | 10 g |
| Lactose | 260 g |
| Crystal cellulose powder | 600 g |
| Corn starch | 350 g |
| Hydroxypropyl cellulose | 100 g |
| CMC—Ca* | 150 g |
| Magnesium stearate | 30 g |
| Total | 1,500 g |

(*carboxymethylcellulose calcium)

The above components were mixed by a usual method and then tabletted to produce 10,000 tablets each containing 1 mg of the active ingredient.

| Formulation Example 2 | |
|---|---|
| Capsules | |
| Compound B4 | 10 g |
| Lactose | 440 g |
| Crystal cellulose powder | 1,000 g |
| Magnesium stearate | 50 g |
| Total | 1.500 g |

The above components were mixed by a usual method and then packed in gelatin capsules to obtain 10,000 capsules each containing 1 mg of the active ingredient.

| Formulation Example 3 | |
|---|---|
| Soft capsules | |
| Compound B 4 | 10 g |
| PEG (polyethylene glycol) 400 | 479 g |
| Saturated fatty acid triglyceride | 1,500 g |
| Peppermint oil | 1 g |
| Polysorbate 80 | 10 g |
| Total | 2,000 g |

The above components were mixed and packed in No. 3 soft gelatin capsules by a usual method to obtain 10,000 soft capsules each containing 1 mg of the active ingredient.

| Formulation Example 4 | |
|---|---|
| Ointment | |
| Compound B4 | 1.0 g |
| Liquid paraffin | 10.0 g |
| Cetanol | 20.0 g |
| White vaseline | 68.4 g |
| Ethylparaben | 0.1 g |
| L-menthol | 0.5 g |
| Total | 100.0 g |

The above components were mixed by a usual method to obtain a 1% ointment.

| Formulation Example 5 | |
|---|---|
| Suppository | |
| Compound B4 | 1 g |
| Witepsol H15* | 478 g |
| Witepsol W35* | 520 g |
| Polysorbate 80 | 1 g |
| Total | 1,000 g |

(*Trademark for triglyceride compound)

The above components were melt-mixed by a usul method and poured into suppository containers, followed by cooling for solidification to obtain 1,000 suppositories of 1 g each containing 1 mg of the active component.

| Formulation Example 6 | |
|---|---|
| Injection formulation | |
| Compound B4 | 1 mg |
| Distilled water for injection formulation | 5 ml |

The formulation is prepared by dissolving the compound in the distilled water whenever it is required.

What is claimed is:

1. A compound of the formula (I):

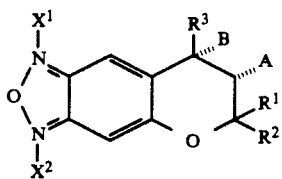

wherein $X^1$ and $X^2$ do not exist or represent oxygen atom;

A represents OH or alkylcarbonyloxy having 1 to 4 carbon atoms;

B represents hydrogen atom; or

A and B together represent a bond;

$R^1$ and $R^2$ are same different from each other and represent hydrogen atom or alkyl group having 1 to 4 carbon atoms, or $R^1$ and $R^2$ together represent 1,2-ethylene, 1,3-propylene, 1,4-butylene or 1,5-pentylene, and these alkylene groups may be substituted by alkyl group having 1 to 4 carbon atoms;

$R^3$ represents amido group of the formula:

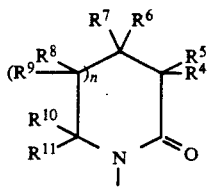

wherein n represent 0 or 1 and $R^4$, $R^5$, $R^6$, $R^7$, $R^8$, $R^9$, $R^{10}$ and $R^{11}$ represent hydrogen atom, alkyl group having 2 to 4 carbon atoms, halogen atom, $ONO_2$, $OSO_3H$, OH, alkyl carbonyloxy having 1 to 4 carbon atoms, alkoxy group having 1 to 4 carbon atoms, or

wherein $R^{12}$ and $R^{13}$ represent hydrogen atom, alkyl group having 1 to 4 carbon atoms or alkylcarbonyl having 1 to 4 carbon atoms, or when n is 1, $R^5$ and $R^6$ or $R^7$ and $R^8$ or $R^9$ and $R^{10}$ represent an optional bond, or when n is 0, $R^5$ and $R^6$ or $R^7$ and $R^{10}$ represent an optional bond, or $R^4$ and $R^5$ or $R^6$ and $R^7$ or $R^8$ and $R^9$ or $R^{10}$ and $R^{11}$ represent an optional=O, with the proviso that not all of $R^4$ to $R^{11}$ are hydrogen, and the pharmacological acceptable salts of the compounds.

2. A compound as claimed in claim 1, wherein $R^1$ and $R^2$ simultaneously represent methyl group.

3. A compound as claimed in claim 2, wherein A represents OH or $OCOCH_3$ or A represents a bond together with B.

4. A compound as claimed in claim 2, wherein A represents OH.

5. A compound as claimed in claim 2, wherein $X^1$ and $X^2$ do not exist.

6. A pharmaceutical composition containing a compound of the formula (I):

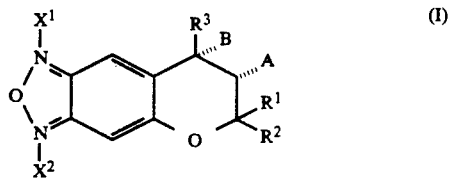

wherein $X^1$ and $X^2$ do not exist or represent oxygen atom;

A represents OH or alkylcarbonyloxy having 1 to 4 carbon atoms;

B represents hydrogen atom;

A and B represent a bond together with each other;

$R^1$ and $R^2$ are same or different from each other and represent hydrogen atom or alkyl group having 1 to 4 carbon atoms, or $R^1$ and $R^2$ together represent 1,2-ethylene, 1,3-propylene, 1,4-butylene or 1,5-pentylene, which may be substituted by alkyl group having 1 to 4 carbon atoms;

$R^3$ represents the formula:

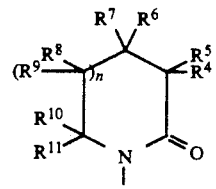

wherein n represents 0 or 1 and $R^4$, $R^5$, $R^6$, $R^7$, $R^8$, $R^9$, $R^{10}$ and $R^{11}$ represent hydrogen atom, alkyl group having 2 to 4 carbon atoms, halogen atom, $ONO_2$, $OSO_3H$, OH, alkyl carbonyl having 1 to 4 carbon atoms, alkoxy group having 1 to 4 carbon atoms, or

wherein $R^{12}$ and $R^{13}$ represent hydrogen atom, alkyl group having 1 to 4 carbon atoms or alkylcarbonyl having 1 to 4 carbon atoms, or when n is 1, $R^5$ and $R^6$ or $R^7$ and $R^8$ or $R^9$ and $R^{10}$ represent an optional bond, or when n is 0, $R^5$ and $R^6$ or $R^7$ and $R^{10}$ represent an optional bond, or $R^4$ and $R^5$ or $R^6$ and $R^7$ or $R^8$ and $R^9$ or $R^{10}$ and $R^{11}$ represent an optional=O, with the proviso that not all of $R^4$ to $R^{11}$ are hydrogen, and the pharmacological acceptable salts of the compounds which can form salts having strong activity for lowering blood pressure.

7. A compound as claimed in claim 1, wherein $R^3$ represents n-(1-oxo-3-methyl-5-bromo) pentyl amino, n-(1-oxo-4,4-dimethyl-5-bromo) pentyl amino, n-(1-oxo-4-methyl-5-bromo) pentyl amino, n-(1-oxo-2-methyl-5-bromo) pentyl amino, n-(1-oxo-4-(R)-(2-methoxyethoxymethyloxy)-5-hydroxyl) pentyl amino, n-(1-oxo-4-(R)-(2-methoxyethoxymethyloxy)-5-bromo) pentyl amino, n-(1-oxo-4-(S)-(2-methoxyethoxymethyloxy)-5-hydroxy) pentyl amino, or n-(1-oxo-4-(S)-(2-methoxy ethoxy methyloxy)-5-bromo) pentyl amino.

8. A pharmaceutical composition as claimed in claim 6, wherein $R^1$ and $R^2$ simultaneously represent methyl group.

9. A pharmaceutical composition as claimed in claim 8, wherein A represents OH or OCOCH$_3$ or A represents a bond together with B.

10. A pharmaceutical composition as claimed in claim 8 wherein A represents OH.

11. A pharmaceutical composition as claimed in claim 8, wherein X$^1$ and X$^2$ do not exist.

12. A pharmaceutical composition as claimed in claim 8, wherein R$^3$ represents n-(1-oxo-3-methyl-5-bromo) pentyl amino, n-(1-oxo-4,4-dimethyl-5-bromo) pentyl amino, n-(1-oxo-4-methyl-5-bromo) pentyl amino, n-(1-oxo-2-methyl-5-bromo) pentyl amino, n-(1-oxo-4-(R)-(2-methoxyethoxymethyloxy)-5-hydroxyl) pentyl amino, n-(1-oxo-4-(R)-(2-methoxyethoxymethyloxy)-5-bromo) pentyl amino, n-(1-oxo-4-(S)-(2-methoxyethoxymethyloxy)-5-hydroxy) pentyl amino or n-(1-oxo-4-(S)-(2-methoxy ethoxy methyloxy)-5-bromo) pentyl amino.

13. A pharmaceutical composition as claimed in claim 6, in a form selected from the group consisting of table, capsule, granule, pill, injection, solution, emulsion, suspension, syrup, and aerosol.

* * * * *